United States Patent [19]

Berg

[11] Patent Number: 5,518,894
[45] Date of Patent: May 21, 1996

[54] RAPID COLIFORM DETECTION SYSTEM

[76] Inventor: James D. Berg, Strandengvn.10, 1390 Vollen, Norway

[21] Appl. No.: 31,154

[22] Filed: Mar. 12, 1993

Related U.S. Application Data

[63] Continuation-in-part of Ser. No. 653,869, Feb. 8, 1991, Pat. No. 5,292,644, which is a continuation of Ser. No. 117,481, Nov. 5, 1987, abandoned.

[51] Int. Cl.$^6$ .............................. C12Q 1/02; C12Q 1/18; C12N 1/12
[52] U.S. Cl. .................... 435/34; 435/4; 435/29; 435/38; 435/968; 435/252.1; 435/252.33
[58] Field of Search ................... 435/29, 4, 34, 435/38, 968, 252.1, 252.33

[56] References Cited

U.S. PATENT DOCUMENTS

| | | | |
|---|---|---|---|
| 3,928,139 | 12/1975 | Dorn | 195/103.5 |
| 4,242,447 | 12/1980 | Findl et al. | 435/39 |
| 4,289,498 | 9/1981 | Baughman | 436/164 |
| 4,340,671 | 7/1982 | Gibson | 435/32 |
| 4,591,554 | 5/1986 | Koumura et al. | 435/18 |
| 4,693,972 | 9/1987 | Mansour et al. | 435/34 |
| 4,777,137 | 10/1988 | Lemonnier | 435/299 |
| 4,923,804 | 5/1990 | Ley | 435/38 |
| 4,925,789 | 5/1990 | Edberg | 435/38 |

FOREIGN PATENT DOCUMENTS

| | | | |
|---|---|---|---|
| 8605206 | 9/1986 | WIPO | C12Q 1/04 |

OTHER PUBLICATIONS

Maddacks, et al. Journal of Clinical Pathology vol. 28, No. 8, pp. 686–687, 1975.

W. R. Bailey, E. G. Scott (1966) Staining Formulae and Procedures, Chapter 37, in *Diagnostic Microbiology*, Mosby Co., St. Louis, pp. 318–319.

*Standard Methods for the Examination of Water and Wastewater*, Seventeen Ed., 1989, American Public Health Association, Washington, D.C., pp. 9–80 to 9–97.

G. C. Geesey, (Nov. 1987) Survival of Microorganisms in Low Nutrient Waters, Chapter 1, in *Biological Fouling of Industrial Waste Water Systems: A Problem Solving Approach*, Water Micro Associates, California, M. W. Mittleman and G. G. Geesey eds., pp. 1–23.

"ColiQuik" Coliform Detection Method of Hach Chemical Co., pp. 112, 113, 119 of Hach Catalog. (undated).

"Colifast" Coliform Monitoring Method by Palintest (Brochure), p. 20. (undated).

B. H. Olson, D. L. Clark, B. B. Milner, M. H. Stewart, and R. L. Wolfe, "Total Coliform Detection in Drinking Water: Comparison of Membrane Filtration with Colilert and Coliquik", *Appl. Env. Micro.*, 57:1535–1539, May 1991.

Primary Examiner—Donald E. Czaja
Assistant Examiner—Jane Williams
Attorney, Agent, or Firm—Dunlap & Codding

[57] ABSTRACT

A rapid presence-absence method for determining if fecal coliform cells are present in a sample. Portions of the original sample are filtered and retained upon microporous filters which are placed in incubation containers having an actuating medium containing a fluorogenic substrate. The samples are incubated for predetermined durations of from about twenty minutes to six hours. After adjusting the pH is incubation to an alkaline level, the containers are irradiated and the fluorescent light emitted is measured. The measured values are adjusted for background fluorescence and corrected for extraneous sources of fluorescence. It is concluded that fecal cells are present in the original sample (i.e., at least one fecal coliform cell per 100 milliliters) when the corrected fluorescence values are positive and meet certain predetermined criteria.

56 Claims, 6 Drawing Sheets

| Sampling<br>(1000 ml Bottle) | Filtration<br>(0.45μm MF) | Rinsing |
|---|---|---|
| Aliquots<br>4 x 100 ml = Duplicate 1<br>4 x 100 ml = Duplicate 2<br>(2x100 ml = 7 h D.C.)<br><br>• Sterile Bottles<br>• Stored at 4°C≤24h<br>• Mixed before aliquots removed & filtered | 4 x 100 ml (Dup. 1)<br>4 x 100 ml (Dup. 2) | 4 x Dup. 1<br>4 x Dup. 2<br>4 x Reagent controls<br><br>• All samples (8)+ controls rinsed 3 x with 20 ml of dilution water |

| Reagent addition (3-10 ml each) | | | Incubation |
|---|---|---|---|
| MEDIA: | BLANK: | CALIBRATION: | All samples, controls, blanks and calibration solutions<br><br>• Sample replicates removed at "0", 2, 4, 6h<br><br>• 44.5°C ± 0.2° |
| All sample replicates (8)<br>4 reagent controls<br><br>• Samples mixed before incubation<br><br>• Note: The 12 control/calibration "tubes" serve all sample bottles (1000 ml) tested in a series | 4 replicates | 4 replicates | |

| Alkaline Developer Addition | Fluorescent Measurements | Signal Interpretation |
|---|---|---|
| • All sample temps must be 44.5°C<br><br>• 33 μl/ml developer<br><br>• Added to all samples, controls, blanks, cal. solutions<br><br>• Mixed before reading | • All sample temps must be approximately 44.5°C<br><br>• "0", 2, 4, 6h readings<br><br>• 2 sample replicates/reading<br><br>• One blank, cal. solution, reagent control per reading | A. If ≥ 20 Net :  +<br>B. If ≤ 20 Net and increasing over 2 consecutive measurements:  +<br>C. If ≤ 20 Net and stable or decreasing:  –<br><br>Note: "20" subject to change<br>Net = Sample avg. less Reagent Control less "0" reading less "0" |
|  | Reading Sequence | 7 h Direct Count |
|  | • 1 Blank 0<br>• 1 calibration 500<br>• 1 Reagent control | • Comparison with P.A. |

FIGURE 1

RAPID COLIFORM DETECTION SYSTEM

CROSS REFERENCE TO RELATED APPLICATION

This is a Continuation-in-Part of U.S. Ser. No. 07/653,869, filed on Feb. 8, 1991, now U.S. Pat. No. 5,292,644, which was a Continuation of U.S. Ser. No. 07/117,481, filed on Nov. 5, 1987, now abandoned.

BACKGROUND

The present invention relates to rapid methods for detecting microorganisms in products for human consumption or use, and, more particularly, but not by way of limitation, to methods for detecting the presence or absence of fecal coliform bacteria in water sources.

Due to numerous reported cases of waterborne diseases, the U.S. EPA promulgated new regulations requiring more stringent monitoring of the hygienic quality of drinking water in 1991. The problem is the same on a world wide basis. In developing countries, it is estimated that 80% of morbidity and 33% of mortality is due to poor hygienic water quality. The result of this has been a substantial development in the market for rapid methods for detecting the hygienic quality of water.

In spite of the acute and immediate need for rapid monitoring and control of water quality, —only minor improvements have been achieved since the introduction of the "Bacterium Coli" as an indicator 70 years ago. Current methodology of the detection of the "coliform group" still generally requires 24–48 hours incubation.

It is evident that industries (water, food, beverage, drug, and energy, for example) which are dependant on using or delivering a safe water quality, require quick response to hygienic variations, so that immediate actions can be taken.

Other market areas are armed forces which need continuous monitoring and verification of safe drinking water quality and protection against bacteriological warfare, both regarding war and natural disaster situations. This is especially critical for military field operations, or civil emergency situations where military personnel are responsible for public health.

Market surveys show that the following market volumes exist for the drinking water industry;

Scandinavia: 650 to 850 000 tests per annum;

EEC: 6 000 to 8 000 000 tests per annum;

World wide: up to 20 000 000 tests per annum.

Market volumes may increase by improved technology, and due to the increased focus on internal quality control in the water industry.

Standard methods for assessing the hygienic quality of water, using either membrane filtration (MF) or Most Probable Number (MPN) techniques, require 24 to 72 hours to complete. It is recognized that the elapsed time is far too long to warn of substandard quality and circumvent debilitating or life-threatening diseases.

According to the reference Standard Methods (American Public Health Association, 1989, *Standard Methods for the Examination of Water and Wastewater,* 17th ed., American Public Health Association, Washington, D.C.) there are a number of rapid methods based upon different principles of detection. The methods generally, however, either lack sensitivity, or require such a long time that the possibility for truly rapid determinations are limited. There is a need therefore for a system which will rapidly detect the presence of fecal coliform bacteria in samples. When used herein, the term "presence" is defined as the occurrence of one or more fecal coliform cells per 100 milliliters of sample.

SUMMARY OF THE INVENTION

The present invention in one version comprises a rapid presence-absence method for concluding when an original liquid or liquified sample contains at least one fecal coliform cell per 100 milliliters. An original sample or liquified sample is divided into portions, for example three portions, and each portion is filtered for retaining microorganisms present in the sample on the filter.

In this manner, a first portion of the original sample is filtered through a first filter, a second portion of the original sample is filtered through a second filter, a third portion of the original sample is filtered through a third filter, and so on.

An actuating medium having a fluorogenic substrate for yielding a fluorescent product is provided. Also provided are sample containers for the first, second, and third samples and control containers for the controls which are run concurrently with the samples. Each container is provided with a predetermined quantity of actuating medium. After the filtering steps, the first filter is placed into the actuating medium contained in the first sample container, the second filter is placed into the actuating medium contained in the second sample container and the third filter is placed into the actuating medium contained in the third sample container.

An incubator which has a heat transference medium which maintains an intimate physical contact with each container disposed therein is provided. The first sample container and the first control container are incubated for a brief first duration. Beginning at approximately the same time, the second sample container and the second control container are incubated for a second duration, and the third sample container and the third control container are incubated for a third duration.

After the brief first duration, the pH of the contents of the first sample container and the contents of the first control container are adjusted to an alkaline pH. Similarly, after the second duration the contents of the second sample container and the contents of the second control container are adjusted to an alkaline pH, and the contents of the third sample container and the contents of the third control container are adjusted to an alkaline pH after the third duration.

After adjusting the pHs of the sample containers and the control containers, the sample and control containers are irradiated with a predetermined excitation wavelength of light. After each irradiation step, a first sample fluorescence value is measured from the first sample container and a first control fluorescence value is measured from the first control container. Similarly, a second sample fluorescence value is measured from the second sample container and a second control fluorescence value is measured from the second control container, and a third sample fluorescence value is measured from the third sample container and a third control fluorescence value is measured from the third control container.

The first control fluorescence value and the first sample fluorescence value are used to obtain a correction factor. Then, the second control fluorescence value is used to adjust the second sample fluorescence value to obtain an adjusted second sample fluorescence value, and the third control fluorescence value is used to adjust the third sample fluorescence value to obtain an adjusted third sample fluorescence value. Following this, the correction factor is used to correct the adjusted second sample fluorescence value to obtain a corrected second sample fluorescence value, and the correction factor is used to correct the adjusted third sample fluorescence value to obtain a corrected third sample fluorescence value.

When both the corrected second sample fluorescence value is positive and the corrected third sample fluorescence value is positive and exceeds the corrected second sample fluorescence value, the conclusion is reached that the original sample contains at least one fecal coliform cell per 100 milliliters.

BRIEF DESCRIPTION OF THE DRAWINGS

FIG. 1 is a schematic showing how a sample is split into aliquots, filtered and incubated at 44.5° C. for detection using the method of the present invention.

DESCRIPTION OF THE PREFERRED EMBODIMENTS

The present invention relies upon the enzymatic hydrolysis of one or both of two fluorogenic substrates (4-methylumbelliferone-β-D-galactoside and 4-methylumbelliferone-β-D-glucuronide) which yields a fluorescent product (4-methylumbelliferone). The rate of hydrolysis or total fluorescence can be quantified using a standard fluorometer.

The method of the present invention can be adapted to use a three-tiered or sequential approach to detect coliform contamination. In this manner, a rapid screening stage can identify a sample of grossly contaminated water within about 20–30 minutes. In the second stage, a sample of less contaminated water can be identified as having fecal coliforms present at a level of at least one fecal coliform cell per 100 ml within one to six hours. Thirdly, direct colony counts are obtained in approximately 7 hours to confirm earlier results. FIG. 1 is a schematic diagram of a method using the second and third stages.

In practice, as few as two samples, but generally from 4 to 10 replicated samples, are filtered and incubated at approximately 4.5° C.±2° C. The samples are removed sequentially after various predetermined incubation times for either rapid screening or presence-absence results. Incubation periods run concurrently in the preferred embodiment. Failure to detect the presence of fecal cells early may effect an optional third analysis of continued incubation of a sample, on agar media, for direct count of microcolonies, until approximately 7 hours of incubation have elapsed. The total elapsed time even for direct counting and including sample filtration and data acquisition generally does not exceed 7 hours.

Figure 2:
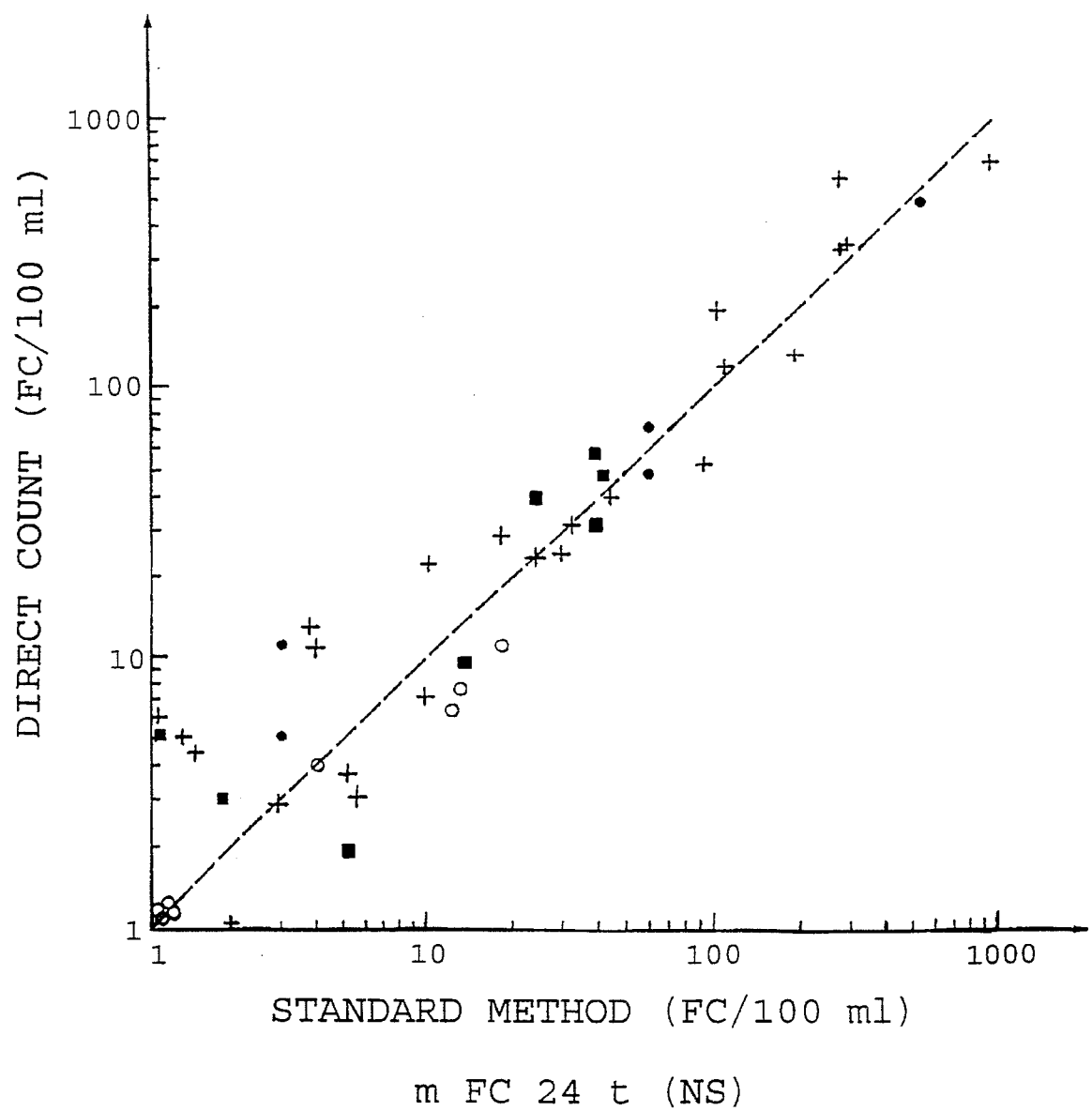
FIG. 2 is a comparison of the 7 hour direct count version of the present invention to the 24 hour m FC Standard Method. The symbols represent different water sources. (+) Nidelva (Trondheim, Norway), (●) Diluted raw sewage (Trondheim, Norway), (■) Akerselva (Oslo, Norway), (o) Water supply, (Kathmandu, Nepal).

FIG. 2 shows the correlation between a 6 hour direct count employing the methods of the present invention and the Standard Methods 24 h m-FC method. Most of the data are derived from tests with Norwegian surface water. The exception to the procedure is the Nepal data which represent a 7 hour incubation owing to high turbidity and/or chlorination. Seven hours is the incubation period of the preferred embodiment of the direct count step.

The present invention in one version comprises a rapid presence-absence method for determining when an original liquid or liquified sample contains at least one fecal coliform cell per 100 milliliters. An original sample or liquified sample is divided into portions, for example three portions, and each portion is filtered for retaining microorganisms present in the sample on the filter.

In this manner, a first portion of the original sample is filtered through a first filter, a second portion of the original sample is filtered through a second filter, a third portion of the original sample is filtered through a third filter, and so on.

An actuating medium having a fluorogenic substrate for yielding a fluorescent product is provided. Also provided are sample containers for the first, second, and third samples and control containers for the controls processed concurrently with the samples. Each container is provided with a predetermined quantity of actuating medium. After the filtering steps, the first filter is placed into the actuating medium contained in the first sample container, the second filter is placed into the actuating medium contained in the second sample container and the third filter is placed into the actuating medium contained in the third sample container.

An incubator which has a heat transference medium which maintains an intimate physical contact with each container disposed therein is provided. The first sample container and the first control container are incubated for a brief first duration. Beginning at approximately the same time, the second sample container and the second control container are incubated for a second duration, and the third sample container and the third control container are incubated for a third duration.

After the brief first duration, the pH of the contents of the first sample container and the contents of the first control container are adjusted to an alkaline pH. Similarly, after the second duration the contents of the second sample container and the contents of the second control container are adjusted to an alkaline pH, and the contents of the third sample container and the contents of the third control container are adjusted to an alkaline pH after the third duration.

After adjusting the pHs of the sample containers and the control containers, the sample and control containers are irradiated with a predetermined excitation wavelength of light. After each irradiation step, a first sample fluorescence value is measured from the first sample container and a first control fluorescence value is measured from the first control container. Similarly, a second sample fluorescence value is measured from the second sample container and a second control fluorescence value is measured from the second control container, and a third sample fluorescence value is measured from the third sample container and a third control fluorescence value is measured from the third control container.

The first control fluorescence value and the first sample fluorescence value are used to obtain a correction factor. Then, the second control fluorescence value is used to adjust the second sample fluorescence value to obtain an adjusted second sample fluorescence value, and the third control fluorescence value is used to adjust the third sample fluorescence value to obtain an adjusted third sample fluorescence value. Following this, the correction factor is used to correct the adjusted second sample fluorescence value to obtain a corrected second sample fluorescence value, and the correction factor is used to correct the adjusted third sample fluorescence value to obtain a corrected third sample fluorescence value.

The determination is made that the original sample contains at least one fecal coliform cell per 100 milliliters when both the corrected second sample fluorescence value is positive and the corrected third sample fluorescence value is positive and exceeds the corrected second sample fluorescence value.

Additionally, the method may further comprise inoculating an agar culture medium with a filtered fourth portion of the original sample, the agar medium containing the actuating medium, then incubating the inoculated culture medium in the incubator for about seven hours. This is followed by irradiating the culture medium with the predetermined excitation wavelength and obtaining a direct count of the number of microcolonies visible on the culture medium. This step may further comprise applying an alkaline solution to the microcolonies for enhancing fluorescence prior to counting the microcolonies.

The brief duration is usually less than about five minutes, and may be about two to five minutes. The second duration may be from about one hour to about five hours. The third duration may be from about two hours to about six hours with the proviso that the third duration is about one hour or more longer than the second duration.

The first duration may be in a range of from about two minutes to about 5 minutes, the second duration about one hour and the third duration about two hours. Additionally, the first duration may be less than about 5 minutes, the second duration about one hour and the third duration in a range of from about two hours to about six hours.

The first duration may be less than about 5 minutes and the second duration about two hours and the third duration about four hours. The first duration may be less than about 5 minutes, the second duration about four hours and the third duration about six hours. The second duration and the third duration may differ by at least about one hour.

In the step of obtaining the correction factor, the correction factor may be obtained by subtracting the first control fluorescence value from the first sample fluorescence value. The adjusted sample fluorescence value may be obtained by subtracting the control fluorescence value from the sample fluorescence value. The corrected sample fluorescence value is then obtained by subtracting the correction factor from the adjusted sample fluorescence value.

In the present invention, the actuating medium may further comprise a nutrient for supporting metabolism of the live fecal coliform cells, an induction agent for inducing the production of an enzyme effective in reacting with the fluorogenic substrate for producing the fluorogenic product, and a surfactant effective in enhancing fluorescence. The induction agent may be lactose, the surfactant effective in enhancing fluorescence may be sodium lauryl sulfate, the enzyme may be β-D-galactosidase, the fluorogenic substrate may be 4-methylumbelliferone-β-D-galactoside, and the fluorescent portion may be 4-methylumbelliferone. The actuating medium may comprise 4-methylumbelliferone-β-D-glucuronide as a second fluorogenic substrate, using β-D-glucuronidase as the enzyme for degrading the second substrate. Preferably, the irradiation step uses an excitation wavelength of about 365 nm which causes an emission wavelength of about 465 nm from the fluorescent product.

The heat transference medium in the incubator may be a liquid such as water or oil, or a solid, such as a metal. When the pH of the containers is adjusted, the adjustment may be made to a pH of above 11 or more preferably, to a pH of about 13.

In another version of the invention, the method may further comprise a fourth portion of the original sample which is filtered and processed as described above for the first, second and third portions. In this version, it is concluded that the original sample contains at least one fecal coliform cell per 100 milliliters when (1) the corrected second sample fluorescence value is positive and the corrected third sample fluorescence value exceeds the corrected second sample fluorescence value, or (2) the corrected third sample fluorescence value is positive and the corrected fourth sample fluorescence value exceeds the corrected third sample fluorescence value.

When a fourth portion is analyzed as described above, the brief duration may be less than about five minutes and may be about two to five minutes. The second duration may be from about one hour to about four hours. The third duration may be from about two hours to about five hours with the proviso that the third duration is about one hour or more longer than the second duration. The fourth duration may be from about three hours to about five hours with the proviso that the fourth duration is about one hour or more longer than the third duration.

In a preferred version, the first duration may be in a range of from about two minutes to about 5 minutes, the second duration about two hours, the third duration about four hours, and the fourth duration about six hours. The first duration may be less than about 5 minutes, the second duration about one to two hours, the third duration in a range of from about three hours to about five hours, and the fourth duration in a range of from about four hours to about six hours with the proviso that the third duration is at least about one hour longer than the second duration and the fourth duration is at least about one hour longer than the third duration. The second duration and the third duration may differ by at least about one hour, the third duration and the fourth duration by at least about one hour, and the second duration and the fourth duration by at least about two hours.

As above, the adjusted sample fluorescence value may be obtained by subtracting the corresponding control fluorescence value from the sample fluorescence value, and the corrected sample fluorescence value further may be obtained by subtracting the correction factor from the adjusted sample fluorescence value.

In either of the versions described above when providing an actuating medium, the actuating medium may be further defined as comprising water, 4-methyl-umbelliferone-β-D-galactoside, about 0.46% to 0.54% by weight of a peptone, about 0.26% to 0.34% by weight of a yeast extract, about 0.4% to 0.6% by weight of an enzyme inducer, about 0.73% to 0.77% by weight of a salt, about 0.48% to 0.52% by weight of pyruvate, about 0.01% to 0.03% by weight of a surfactant, and about 0.009% to 0.011% by weight of bile salts. The enzyme inducer may be lactose, the surfactant sodium lauryl sulfate, and the salt NaCl. The actuating medium may further comprise about 0.004% to 0.006% by weight of 4-methylumbelliferone-β-D-glucuronide.

In another version of the present invention as described in detail above, the second sample container and the second control container is incubated for a duration of about 20 to 30 minutes. A conclusion is reached that the original sample contains at least one fecal coliform cell per 100 milliliters (i.e. "presence" is verified) when the corrected second sample fluorescence value is positive. A further conclusion may be reached in this case that the original sample contains at least 25 fecal coliform cells per 100 milliliters. In this version the brief first duration may be less than about five minutes, and it may be from about two to about five minutes.

In another version of the present invention as described in detail above, second sample container and the second control container may be incubated for a second duration of about one hour. The conclusion may be reached that the original sample contains at least one fecal coliform cell per 100 milliliters when the corrected second sample fluorescence value corresponds to a molarity of 4-methylumbelliferone in second sample of at least about 0.01 μmolar.

In all versions of the present invention, the composition of matter used in determining if an original liquid or liquified sample contains at least one fecal coliform cell per 100 milliliters may comprise an aqueous mixture of water, 4-methyl-umbelliferone-β-D-galactoside and a dry medium. The aqueous mixture, may further comprise about 0.46% to 0.54% by weight of a peptone, about 0.26% to 0.34% by weight of a yeast extract, about 0.4% to 0.6% by weight of an enzyme inducer, about 0.73% to 0.77% by weight of a salt, about 0.48% to 0.52% by weight of pyruvate, about 0.01% to 0.03% by weight of a detergent, and about 0.009% to 0.011% by weight of bile salts.

The peptone may be proteose peptone No. 3, the enzyme inducer lactose, the salt NaCl and the detergent sodium lauryl sulfate. The medium added to the mixture may further comprise 4-methylumbelli-ferone-β-D-glucuronide as a second fluorogenic substrate. The mixture may further comprise about 0.004% to 0.006% by weight of 4methylumbeoferpme-β-D-glucurondie.

The composition for mixing with water and with an amount of 4-methylumbelliferone-β-D-galactoside may comprise in dry form about 17% to 21% by weight of a peptone, about 10% to 14% by weight of a yeast extract, about 15% to 24% by weight of an enzyme inducer, about 28% to 30% by weight of a salt, about 18% to 21% by weight of pyruvate, about 0.3% to 1.2% by weight of a detergent, and about 0.3% to 0.5% by weight of bile salts. The peptone may be proteose peptone No. 3, the enzyme inducer lactose, the salt NaCl and the detergent sodium lauryl sulfate. The medium may further comprise 4-methylumbelliferone-β-D-glucuronide as a second fluorogenic substrate, and the 4-methylumbelliferone-β-D-glucuronide may comprise about 0.1% to 0.3% by weight of the medium.

EXAMPLES

FIG. 1 represents a schematic version of the present invention in which a 1000 ml original liquid sample is divided into ten approximately equal portions. Each of these 100 ml portions is filtered through a microporous filter such as a 0.45μm Millipore filter. Two of the filters may be placed on nutrient agar cultures containing the actuating medium as disclosed herein. The other eight filters are placed in containers containing approximately 5–10 ml of liquid actuating medium. The eight sample containers (and the culture plates, if used) are placed in an incubator, such as a water bath, for approximately 44.5° C.±2° C. Controls containing the actuating, or reagent, medium are incubated simultaneously. Simultaneously, blank containers (containing only blank media) and calibration standards (containing blank media and 4-methylumbelliferone) are incubated.

Pairs of sample containers are removed at predetermined intervals or durations during the incubation period. The first incubation duration is brief and is generally about two to five minutes. This may also be referred to as the "zero sample". This brief period allows extraneous fluorescent materials already present in the filter or in the cells in the sample to leach into the medium, but is too short for fecal coliform cells in the medium to begin significant production of 4-methylumbelliferone. Additional pairs of replicates are removed after predetermined intervals, such as two, four and six hours, of incubation. After incubation, an alkaline solution such as NaOH is added to the sample to cause an increase in the sensitivity of the detection of 4-methylumbelliferone. The samples are then irradiated, then analyzed for fluorescence emission. A blank container, calibration standard and reagent control are also processed and irradiated at each time interval for comparison purposes.

Data are analyzed after all samples have been incubated, irradiated and detected for fluorescence. The fluorometer is recalibrated at each step with the blank container and calibration container.

A sample fluorescence value is determined for each interval or duration by averaging the two sample replicates. The fluorescence value obtained from the reagent control incubated for that particular duration is subtracted from the sample fluorescence value to obtain an adjusted sample fluorescence value. When this algorithm is carried out for the "zero sample", the adjusted fluorescence value is a "correction factor" which is then applied to samples incubated for longer durations. Each adjusted sample fluorescence value is corrected by subtracting from it the correction factor, to obtain a corrected sample or "net" fluorescence value.

In this version of the invention, if the two hour corrected fluorescence (net) value is positive, and if the four hour corrected fluorescence value is positive and is greater than the two hour value, it is concluded that fecal coliform cells are present in the original sample (i.e. ≧one fecal coliform cell/100 ml).

If the four hour corrected fluorescence value is positive, and if the six hour corrected fluorescence value is positive and is greater than the four hour value, it is concluded that fecal coliform cells are present in the original sample (i.e. ≧one fecal coliform cell per 100 ml).

Figure 3:
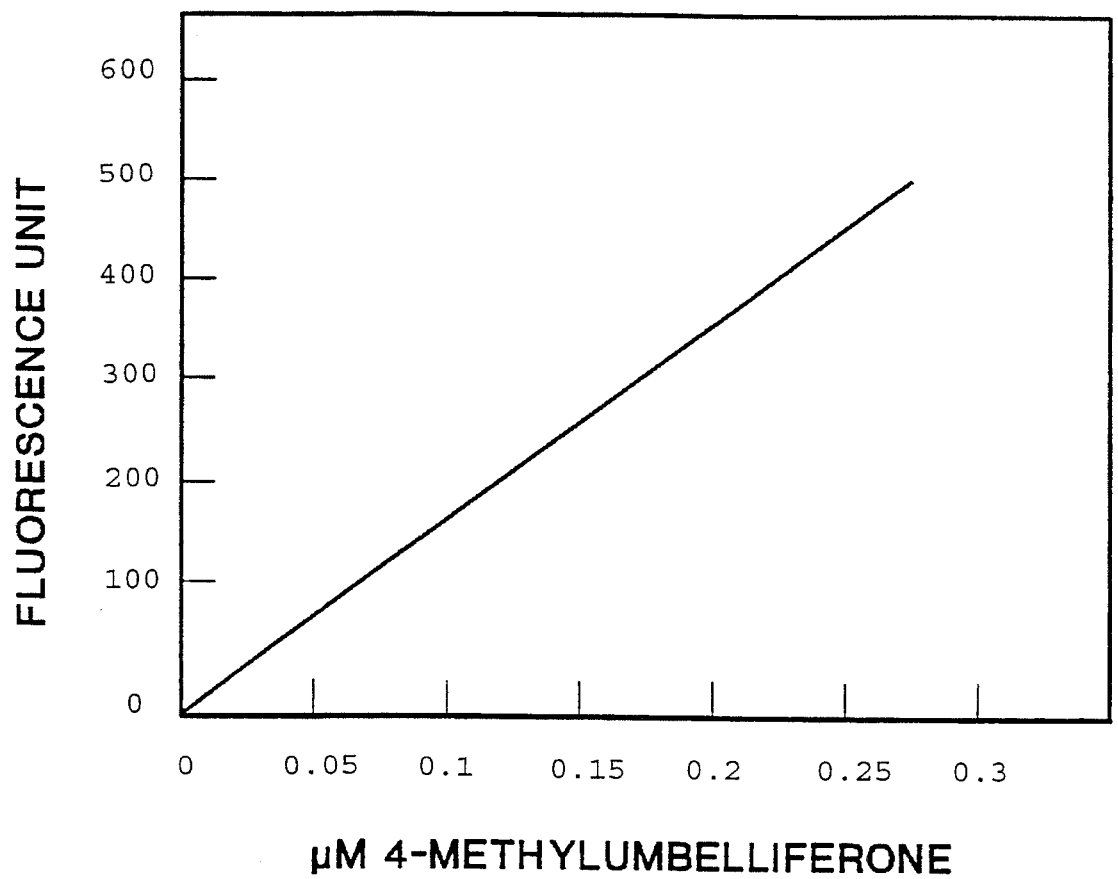
FIG. 3 is a graph showing a correlation between 4-methylumbelliferone concentration and units of fluorescence.

If a corrected sample fluorescence value corresponds to a molarity of at least about 0.01 μm of 4-methylumbelliferone in the sample in any of the corrected samples, it is concluded that fecal coliform cells are present in the original sample (i.e. ≧one fecal coliform cell per 100 ml). FIG. 3 shows a correlation curve with molarity of 4-methylumbelliferone plotted against a standard calibrated fluorescence scale.

If there are no two consecutively increasing corrected fluorescence values, or if the corrected value fails to correspond to a molarity of at least about 0.01 μm of 4-methylumbelliferone after six hours, it is concluded that fecal coliform cells are not present in the original sample, (i.e. the concentration fecal cells is < one fecal coliform cell per 100 ml).

The culture plate samples may be analyzed after a 7 hr. incubation period to confirm the conclusion.

Methods

Filtration

A sample of liquid to be tested, such as a source of potential drinking water, is provided. The sample is filtered in accordance with the membrane filtration procedure published in Section 9222D, of *Standard Methods For the Examination of waste and Wastewater*, 17th Ed., American Public Health Association, 1989, which is hereby incorporated herein by reference.

Screening or Presence-Absence Methods

Figure 4:
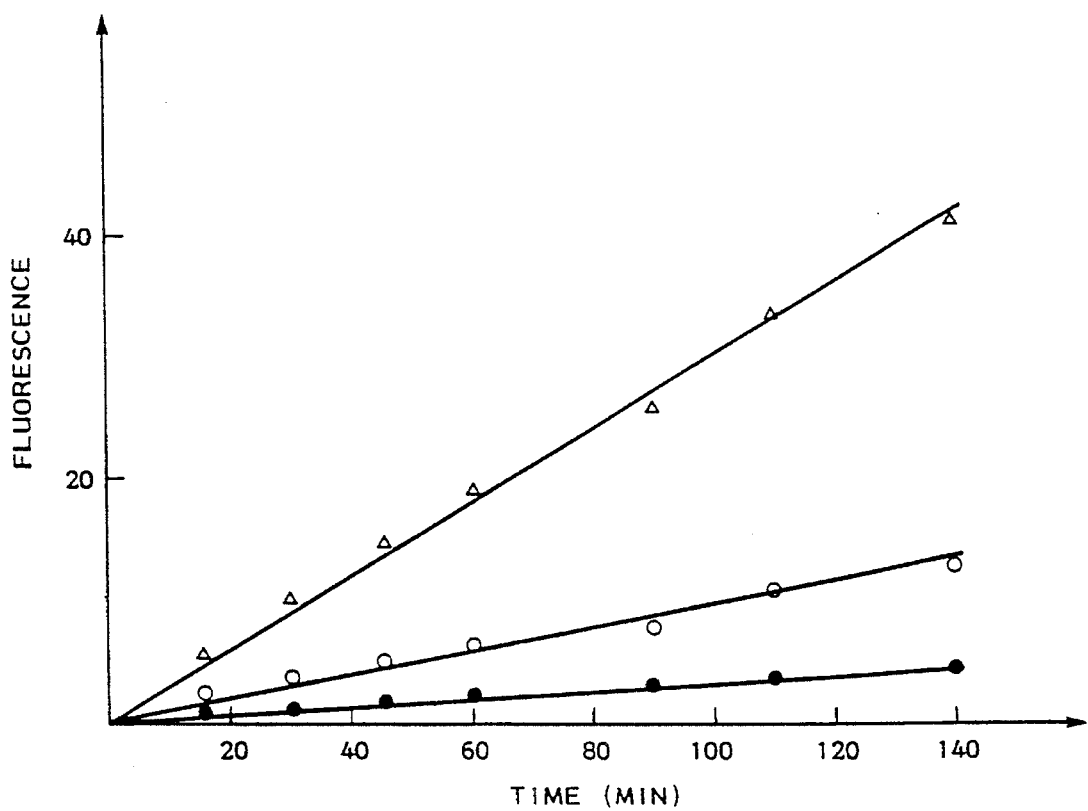
FIG. 4 is a graph showing the production of MU from 4-MU-β-D-galactoside by coliform bacteria in drinking water contaminated with raw sewage (●); after addition of lactose enhanced induction of β-D-galactosidase (o), and after addition of sodium lauryl sulfate, a detergent, which further enhanced activity (Δ). Enzyme assay temperature was 41.5° C.

For the screening step or the presence-absence step, the filter is deposited into the sample container containing actuating media. Actuating media contains lactose, and a detergent, sodium lauryl sulfate shown here to enhance fluorescence of 4-methylumbelliferone (FIG. 4). The filter is placed along the wall of the incubation tube such that it is submerged by the media.

The tubes are incubated in an incubator such as a water bath at approximately 44.5° C.+2° C. and are removed from the water bath just prior to irradiation and fluorescence measurement. The tube containing the sample is irradiated using the UV-light source set at a predetermined wavelength. Samples measured for presence-absence are measured at predetermined time intervals such as every hour or at one, two, four and six hours after initiation of incubation. Samples to be screened are incubated for approximately 20–30 minutes prior to irradiation and fluorescence measurement. For measurement in a standard fluorometer 3–10 ml sample are combined with about 33 μl of 10M NaOH per ml of reagent.

Prior to the first reading, the fluorometer is prepared and calibrated by first warming up the blank and Internal Calibration Standard (working solution) to 44.5° C. The instrument is first adjusted to zero (zero knob) with 3 ml Blank media (without MUGal) mixed with 100 μl 10M NaOH then it is adjusted to 500 (span knob) with 3 ml internal standard (0.27 μm MU) mixed with 100 μl 10M NaOH. Gain is set at 1000. A standard fluorometer obtained from Sequoia Turner, Model 450-003, was used.

In the preferred embodiment, the incubator is a water bath. However, the incubator can be any apparatus which can maintain a stable incubating temperature and which has a heat transference medium which maintains an intimate physical contact with the container surface. This includes incubators with liquid media such as water or oil, and block or sink incubators having a solid or metal heat transference medium.

Direct count Method

In the direct count method, the filter is deposited upon the surface of the direct count media on a direct count plate. The prepared culture plates are placed in waterproof plastic bags, submerged in the water bath, and incubated for about 7 h±15 min. at 44.5+0.2° C. It is important to ensure that the petri dishes are submerged to maintain stable temperature requirements.

After the incubation period, the culture plates are removed from the incubator and are irradiated with UV light, such as is commercially available from UVP, Inc. (Model No. UVL-21) at a predetermined wavelength. The plates are then observed for fluorescing microcolonies. Preferably, an alkaline developer such as NaOH can be sprayed over the filter and the number of blue fluorescent colonies are counted. Any colonies desired to be tested for confirmation must be removed prior to addition of the alkaline developer.

Equipment and Supplies

Equipment and Supplies used in the 7 Hour Direct Count Method include a membrane filtration apparatus (such as is available from Sartorius), a water bath incubator able to hold a temperature constant about 44.5° C.±0.2° C. such as is available from HaakeModel SWB20, a longwave UV hand-held lamp (e.g. available from UVP, Inc., UVL-21), actuating media, alkaline developer solution, dilution water (e.g., 0.1% sterile peptone), plastic petri dishes, membrane filters (e. g., Millipore 0.45 μm with grid), 4-methylumbelliferone-β-D-galactoside (MUGal), 95% ethanol, and sodium lauryl sulfate.

Equipment and supplies used in the screening or presence-absence tests include a membrane filtration apparatus, a water bath incubator able to hold a temperature constant about 44.5° C., a longwave UV hand-held lamp, actuating media, dilution water (e. g., 0.1% sterile peptone), membrane filters (e.g., 0.45 μm with grid), 4-methylumbelliferone-β-D-galactoside (MUGal), 95% ethanol, sodium lauryl sulfate, a fluorometer, Blank media, a solution of 10M NaOH, sterile incubation tubes, and 4-methylumbelliferone (4-MU).

Preparation of 0.02% Sodium Lauryl Surfate (SLS) Solution

Dissolve 0.1 g sodium lauryl sulfate in 500 ml distilled water. Autoclave at 120° C. for 15 minutes.

Preparation of 4-MU-β-D-galactoside Substrate Solution

Add 1.5 ml 95% ethanol to 0.0375 g MUGal and shake vigorously for 2 minutes. Then, add 28.5 ml 0.02% sterile SLS (sodium lauryl sulfate) and mix well. Heat tube with the substrate solution at 60°–80° C. until dissolved. Preferably, this is prepared freshly for each test.

Preparation of Plates for Direct counts

Rehydrate 12.925 g actuating media in 500 ml sterile distilled water. Adjust the pH at 20° C. to 7.3. Add 5.0 g agar to the media and heat to near boiling to dissolve agar. Remove from heat and cool to about 70° C. and add 20 ml MUGal solution to the media. Cool the media to 45°–50° C. Dispense 5 to 7 ml into a plastic petri dish to produce the direct count plate. Store finished media at 4° C. and discard any unused media after 14 days, preferably.

Preparation of Liquid Actuating Media

Rehydrate 12.925 g of an actuating media (preferred composition shown in Table 1) in 500 ml sterile distilled water. Adjust the pH at 20° C to 7.3. Heat the media to near boiling and remove from heat. Cool to about 70° C. and add 20 ml of MUGal solution to the media. Cool the media to below 45° C. Pipette about 15 ml of media into a sterile tube to produce a sample container.

TABLE 1

| Actuating Media | Dry Weight (approx.) | % Weight When Rehydrated |
|---|---|---|
| Actuating Media composition | | |
| Protease peptone no. 3 | 2.5 g ± 0.2 | .46–.54 |
| Yeast extract | 1.5 g ± 0.2 | .26–.34 |
| Lactose | 2.5 g ± 0.5 | .4–.6 |
| NaCl | 3.75 g ± 0.1 | .73–.77 |
| Pyruvate | 2.5 g ± 0.1 | .48–.52 |
| Sodium lauryl sulphate | 0.10 g ± 0.05 | .01–.03 |
| Bile salts | 0.05 g ± 0.005 | .009–.011 |
| 4-methylumbelliferone-β-D-glucuronide | 0.025 g ± 0.005 | .004–.006 |

Preparation of Blank Media

Rehydrate 25.80 g Blank media (preferred composition shown in Table 2) in 1000 ml sterile distilled water. Adjust the pH at 20° C. to 7.3 and filter-sterilize the media.

TABLE 2

Blank Media Composition

| Blank Media | Dry Weight | % Weight When Rehydrated |
|---|---|---|
| Protease peptone no. 3 | 5.0 g ± 0.4 | .46–.54 |
| Yeast extract | 3.0 g ± 0.4 | .26–.34 |
| Lactose | 5.0 g ± 1.0 | .4–.6 |
| NaCl | 7.5 g ± 0.2 | .73–.77 |
| Pyruvate | 5.0 g ± 0.2 | .48–.52 |
| Sodium lauryl sulphate | 0.2 g ± 0.1 | .01–.03 |
| Bile Salts | 0.1 g ± 0.01 | .009–.011 |

Preparation of Internal Calibration Standard

First prepare a 68.1 µm MU stock solution by dissolving 6 mg of 4-MU in 500 ml of Blank media (without MUGal). Prepare fresh stock solution each second week. Dilute 1 ml of the stock solution to 250 ml with Blank media to prepare a Working solution (0.27 µm MU). This is used as the calibration standard. Fresh working solution is preferably prepared each week.

The screening, presence-absence and direct count methods can be performed separately, simultaneously, or sequentially, depending on the information desired by the tester. For example, the screening method could be used alone to screen a large number of water samples for high contamination. The presence-absence method could be used to further identify water samples having questionable coliform levels. The direct count method could be used separately to confirm the presence of fecal coliforms in particular water samples. The methods could also be used in combination. For example, a water sample could be tested simultaneously by both the screening method and the presence-absence method, by the screening method and the direct count method, or by the presence-absence method and the direct count method. Finally, a sample could be tested by simultaneously conducting the screening method, the presence-absence method, and the direct count method.

The results of the present invention are demonstrated by the following data sets.

Data Set 1

Naturally occurring populations of fecal coliform bacteria in a U.S. surface waters were assessed both using a version of the invention and using the Standard Methods m-FC 24h method. Water from the Monocacy River, Md., USA, was collected on Mar. 26, 1992 and analyzed for fecal coliforms using the invention. Methods were as described above.

Three dilutions were tested in duplicate. Samples were incubated as above. The m-FC samples were counted at 24h. The fluorescence in the rapid detection method samples was measured at "zero time", 2, 4 and 6 hours using a Turner Model 450-003 fluorometer. The excitation and emission wavelengths were 365, and 465 nm, respectively.

Results and Discussion

Figure 5:
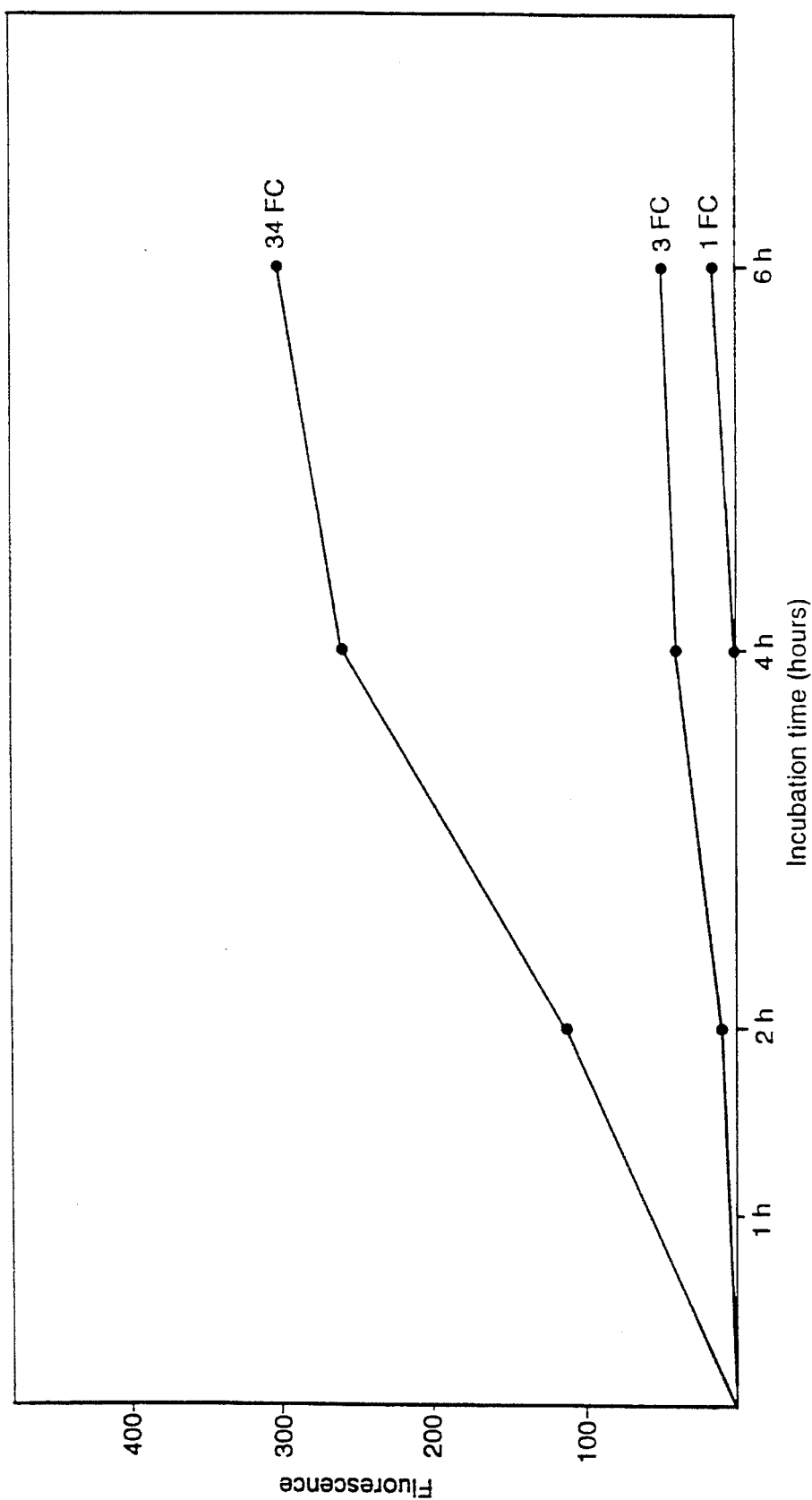
FIG. 5 is a graph showing an example of incubation time versus fluorescence for samples at three fecal coliform cell concentrations.

The results are shown in FIG. 5. All dilutions corresponding to 1, 3, and 34 FC/100 ml yield a positive (+) result indicating presence of fecal bacteria. The lowest count, 1 FC/100 ml, was detected as positive at 6 h, 3 FC/100 ml was detected as positive after 2 hours, and 34 FC/100 ml at $\leq 2$ hours, the first measurement time. In this example therefore, in the lowest count, presence was verified in 6 hours. In the next lowest count (3 FC/100 ml), presence was verified in 2 hours and in the highest count (34 FC/100 ml), presence was verified in 2 hours and probably would have been verified in as little as 20 minutes if a measurement had been taken then.

Data Set 2

Figure 6:
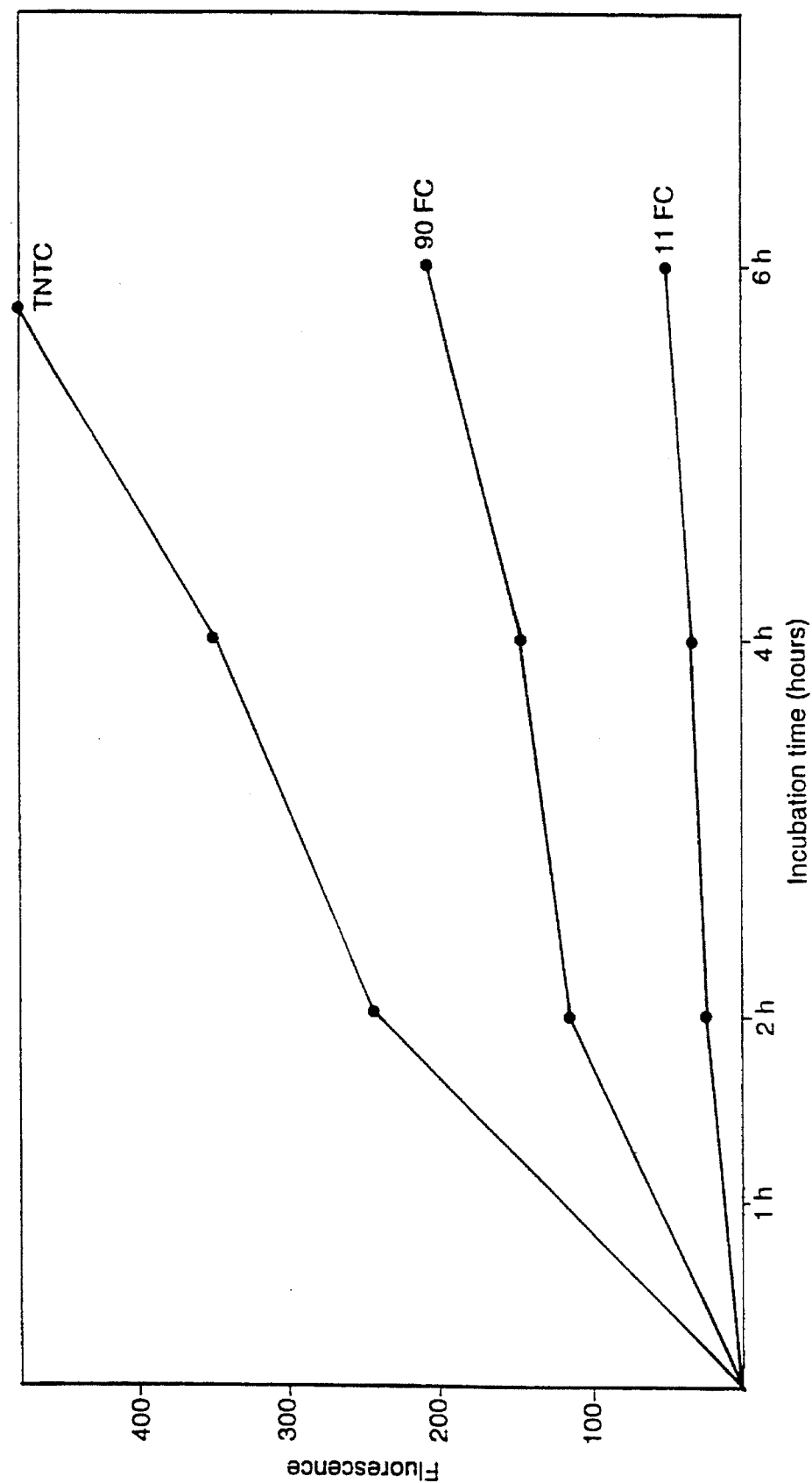
FIG. 6 is another graph showing an example of incubation time versus fluorescence for samples at three fecal coliform cell concentrations.

Natural populations of fecal coliform bacteria in a Norwegian surface water with and without sewage contamination were analyzed in this example using a version of the present invention and the standard m-FC 24h method. Water from the Aker River in Oslo, Norway, was collected on Apr. 3, 1992 and analyzed for fecal coliforms using the invention. Three samples were tested: the river water, and river water with two different doses of raw domestic sewage. Samples, prepared as described above, were incubated in a water bath at 44.5° C. The m-FC samples were counted at 24 h. The fluorescence in the rapid detection method samples were measured at "zero time" 2, 4 and 6 hours using a Turner Model 450-003 fluorometer. The excitation and emission wavelengths were 365 and 465 nm, respectively. The results are shown in FIG. 6. All three samples corresponding to 11, 90, and TNTC yielded a positive (+) result, verifying the presence of fecal coliform bacteria. All results were positive within $\leq 2$ hours. Had measurements been taken after a one hour incubation interval, the TNTC cells/100 ml and 90 cells/100 ml samples would likely have been verified as positive. The 11 cell sample would have been verified as positive as early as after 1.5 hrs. of incubation.

Data Set 3

Naturally occurring populations of fecal coliform bacteria in several surface waters were analyzed in this example using the version of the present invention and the standard m-FC 24 hour method. Fresh samples from the Monocacy River, Aker River and Loysa River, were collected and analyzed daily. Also, one sample of "worst case" water was prepared according to an EPA Guide, Standard and Protocol for Testing Microbiological Water Purifiers (1987). The physical parameters and composition of the samples are shown in Table 3.

TABLE 3

Composition of the Test Samples

| | Sample Source | | | |
|---|---|---|---|---|
| Parameter | Monocacy River* | "Worst Case" Water | Aker River | Loysa River |
| Turbidity (NTU) | 13–14 | 39 | — | — |
| TDS (mg/l) | 177–183 | 1500 mg/l | — | — |
| Conductivity (µmhos) | 253–262 | — | — | — |
| pH | 7.34–7.45 | 7.4 | 7.2 | 6.5–6.8 |
| Temperature (°C.) | 8 | — | 8 | 17 |
| Humic acid (added) mg/l | — | 10 | — | — |

*Range of values for 2 test days

All samples were tested in duplicate. Samples were incubated in a water bath at 44.5° C. and prepared as discussed above. The m-FC samples were counted at 24h. The fluorescence in the rapid detection method samples was measured at "zero time", 2, 4, and 6 hours using a Turner Model 450-003 fluorometer. The excitation at emission wavelengths were 365 and 465 nm respectively.

The results are summarized in Table 4. Presence/absence determinations of fecal coliforms using the method of the present invention are shown as ±. The corrected fluorescence value (scale of 0 to 500) and earliest positive "presence" detection time (2 to 6 h) are reported.

TABLE 4

| Sample Identification | Sample No. | Present Invention | | | 7 h Direct Count | Standard Methods m FC 24 h |
| --- | --- | --- | --- | --- | --- | --- |
| | | Liquid Media Method (P/A) | | | | |
| | | +/− | Fluor. Value | Detection time (h) | | |
| Monocacy River (I) 3-25-92 | 1 | + | 236 | 2 | 40 | 52 |
| | 2 | + | 50 | 2 | 2 | 4.3 |
| | 3 | + | 26 | 2 | 0.5 | 0 |
| Monocacy River (II) 3-26-92 | 4 | + | 113 | 2 | 40 | 42 |
| | 5 | + | 16 | 2 | 3 | 4.3 |
| | 6 | + | 10 | 6 | 1 | 0 |
| "Worst Case" Water 3-25-92 | 7 | + | 86 | 2 | 24 | — |
| | 8 | + | 5 | 6 | 6.5 | 9 |
| | 9 | − | 0 | 6 | 0.5 | 1 |
| Aker River (I) 4-03-92 | 10 | + | 244 | 2 | TNTC | — |
| | 11 | + | 117 | 2 | 90 | 72 |
| | 12 | + | 24 | 2 | 11 | 7 |
| Aker River (II) 4-07-92 | 13 | + | 31 | 2 | 8 | 15 |
| | 14 | + | 21 | 4 | 4 | 4 |
| Aker River (III) 3-04-93 | 15 | + | 39 | 2 | — | 150 |
| | 16 | − | 0 | 6 | — | 0 |
| | 17 | − | 10 | 6 | — | 0.5 |
| Loysa River Waterwork 5-26-92 | 18 | − | 0 | 6 | 0 | 0 |

A positive result for all samples having >10 FC/100 ml was measured in ≤2 hours (Samples 1, 4, 7, 10, 11, 12, and 15). Samples containing 1–10 FC/100 ml were positive in 2–6 hours (Samples 2, 5, 6, 8, 13 and 14). Also, the 7h direct count shows close agreement with the standard m-FC 24h count in all cases. TNTC when used herein means "Too Numerous To Count".

All patents or publications cited herein are hereby incorporated herein by reference.

Changes may be made in the embodiments of the invention described herein or in parts of the elements of the embodiments described herein or in the steps or in the sequence of steps of the methods described herein without departing from the spirit and scope of the invention as defined in the following claims.

What is claimed is:

1. A rapid presence-absence method for determining when an original liquid or liquified sample contains less than one fecal coliform cell per milliliters, comprising:
   (a) filtering a first portion of the original sample upon a first filter for concentrating the live fecal coliforms in the first portion and filtering a second portion of the original sample upon a second filter for concentrating the live fetal coliform cells in the second portion;
   (b) providing an actuating medium having a fluorogenic substrate which when metabolized by β-galactosidase yields a fluorescent product;
   (c) providing a first sample container and a second sample container;
   (d) exposing the first filter to a first quantity of the actuating medium in the first sample container and exposing the second filter to a second predetermined quantity of the actuating medium in the second sample container;
   (e) providing an incubation means;
   (f) incubating a first sample container for a first duration and the second sample container for a second duration, wherein a first duration is in a range of from about one to five hours and the second duration is in the range of from about two to six hours and with the proviso that a second duration is at least about one hour longer than the first duration;
   (g) adjusting a pH of the contents of the first sample container to an alkaline pH after the first duration;
   (h) irradiating the first sample container, after adjusting the pH, with an excitation wavelength of light;
   (i) adjusting the pH of the contents of the second sample container to an alkaline pH after the second duration;
   (j) irradiating the second sample container after adjusting the pH, with the excitation wavelength of light;
   (k) measuring, after each irradiation step, a first sample fluorescence value from the first sample container and a second sample fluorescence value from the second sample container;
   (l) correcting the first sample fluorescence value to obtain a corrected first sample fluorescence value;
   (m) correcting the second sample fluorescence value in a predetermined manner to obtain a corrected second sample fluorescence value; and
   (n) concluding that the original sample contains less than one fecal coliform cell per 100 milliliters when the corrected first sample fluorescence value is positive and the corrected second sample fluorescence value is positive and is less than or equal to the corrected first sample fluorescence value.

2. The method of claim 1 further comprising culturing at least a third portion of the original sample on an agar medium containing the actuating medium, incubating the culture medium in the incubation means for about seven hours, irradiating the culture medium after the incubation period with the excitation wavelength and counting a number of microcolonies visible on the culture medium.

3. The method of claim 2 further comprising applying an alkaline solution to the microcolonies for enhancing fluorescence prior to counting the microcolonies.

4. The method of claim 1 wherein the actuating medium further comprises:

(1) a nutrient for supporting metabolism of the live fecal coliform cells, (2) an induction agent for inducing a production of an enzyme effective in reacting with the fluorogenic substrate for producing the fluorogenic product, and (3) a surfactant effective in enhancing fluorescence.

5. The method of claim 4, wherein the induction agent is lactose, the surfactant effective in enhancing fluorescence is sodium lauryl sulfate, the enzyme is β-D-galactosidase, the fluorogenic substrate is 4-methylumbelliferone-β-D-galactoside, and the fluorescent portion is 4-methylumbelliferone.

6. The method of claim 5 wherein the medium further comprises 4-methylumbelliferone-β-D-glucuronide as a second fluorogenic substrate.

7. The method of claim 1 wherein the irradiation step uses an excitation wavelength of about 365 nm which causes an emission wavelength of about 465 nm.

8. The process of claim 1 wherein the step of providing an incubation means further comprises providing a liquid heat transference medium therein.

9. The process of claim 8 wherein the liquid heat transference medium is water.

10. The process of claim 8 wherein the liquid heat transference medium is an oil.

11. The process of claim 1 wherein the step of providing an incubation means further comprises providing a solid heat transference medium therein.

12. The process of claim 11 wherein the solid heat transference medium in the incubation means is a metal.

13. The method of claim 1 wherein the alkaline pH is above 11.

14. The method of claim 13 wherein the alkaline pH is about 13.

15. A rapid presence-absence method for determining when an original liquid or liquified sample contains less than one fecal coliform cell per 100 milliliters, comprising:

(a) filtering a first portion of the original sample upon a first filter for concentrating the live fecal coliforms in the first portion and filtering a second portion of the original sample upon a second filter for concentrating the live fecal coliform cells in the second portion and filtering a third portion of the original sample upon a third filter for concentrating the live fecal coliform cells in the third portion;

(b) providing an actuating medium having a fluorogenic substrate which when metabolized by β-galactosidase yields a fluorescent product;

(c) providing a first control container, a second control container, and a third control container, each containing a predetermined quantity of actuating medium therein;

(d) exposing the first filter to a first predetermined quantity of the actuating medium in a first sample container, exposing the second filter to a second predetermined quantity of the actuating medium in a second sample container and exposing the third filter to a third predetermined quantity of the actuating medium in a third sample container;

(e) providing an incubation means;

(f) incubating the first sample container and the first control container for a brief first duration;

(g) adjusting the pH of the contents of the first sample container and the contents of the first control container to an alkaline pH after the brief first duration;

(h) irradiating the first sample container and the first control container, after adjusting the pH, with a predetermined excitation wavelength of light;

(i) incubating the second sample container and the second control container for a second duration;

(j) adjusting the pH of the contents of the second sample container and the contents of the second control container to an alkaline pH after the second duration;

(k) irradiating the second sample container and the second control container, after adjusting the pH, with the predetermined excitation wavelength of light;

(l) incubating the third sample container and the third control container for a third duration;

(m) adjusting the pH of the contents of the third sample container and the contents of the third control container to an alkaline pH after the third duration;

(n) irradiating the third sample container and the third control container, after adjusting the pH, with the predetermined excitation wavelength of light;

(o) measuring, after each irradiation step, a first sample fluorescence value from the first sample container and a first control fluorescence value from the first control container, a second sample fluorescence value from the second sample container and a second control fluorescence value from the second control container, and a third sample fluorescence value from the third sample container and a third control fluorescence value from the third control container;

(p) using the first control fluorescence value and the first sample fluorescence value to obtain a correction factor;

(q) using the second control fluorescence value to adjust the second sample fluorescence value to obtain an adjusted second sample fluorescence value;

(r) using the third control fluorescence value to adjust the third sample fluorescence value to obtain an adjusted third sample fluorescence value;

(s) using the correction factor to correct the adjusted second sample fluorescence value to obtain a corrected second sample fluorescence value;

(t) using the correction factor to correct the adjusted third sample fluorescence value to obtain a corrected third sample fluorescence value; and (u) concluding that the original sample contains less than one fecal coliform cell per 100 milliliters when the corrected second sample fluorescence value is positive and the corrected third sample fluorescence value is positive and is less than or equal to the corrected second sample fluorescence value.

16. The method of claim 15 further comprising culturing a fourth portion of the original sample on an agar medium containing the actuating medium, incubating the culture medium in the incubation means for about seven hours, irradiating the culture medium after the incubation period with the excitation wavelength and counting a number of microcolonies visible on the culture medium.

17. The method of claim 16 further comprising applying an alkaline solution to the microcolonies for enhancing fluorescence prior to counting the microcolonies.

18. The method of claim 15 wherein the brief duration is less than about five minutes.

19. The method of claim 18 wherein the first duration is about two to five minutes.

20. The method of claim 15 wherein the second duration is from about one hour to about five hours.

21. The method of claim 15 wherein the third duration is from about two hours to about six hours with a proviso that third duration is about one hour or more longer than the second duration.

22. The method of claim 15 wherein the first duration is in a range of from about two minutes to about 5 minutes, the second duration is about one hour and the third duration is about two hours.

23. The method of claim 15 wherein the first duration is less than about 5 minutes, the second duration is about one hour and the third duration is in a range of from about two hours to about six hours.

24. The method of claim 15 wherein the first duration is less than about 5 minutes, the second duration is about two hours and the third duration is about four hours.

25. The method of claim 15 wherein the first duration is less than about 5 minutes, the second duration is about four hours and the third duration is about six hours.

26. The method of claim 15 wherein the second duration and the third duration differ by at least about one hour.

27. The method of claim 15 wherein the step of obtaining the correction factor further comprises subtracting the first control fluorescence value from the first sample fluorescence value.

28. The method of claim 15 wherein the step of obtaining an adjusted second sample fluorescence value further comprises subtracting the second control fluorescence value from the second sample fluorescence value.

29. The method of claim 15 wherein the step of obtaining a corrected second sample fluorescence value further comprises subtracting the correction factor from the adjusted second sample fluorescence value.

30. The method of claim 15 wherein the actuating medium further comprises:

(1) a nutrient for supporting metabolism of the live fecal coliform cells, (2) an induction agent for inducing the production of an enzyme effective in reacting with the fluorogenic substrate for producing the fluorogenic product, and (3) a surfactant effective in enhancing fluorescence.

31. The method of claim 30, wherein the induction agent is lactose, the surfactant effective in enhancing fluorescence is sodium lauryl sulfate, the enzyme is β-D-galactosidase, the fluorogenic substrate is 4-methylumbelliferone-β-D-galactoside, and the fluorescent portion is 4-methylumbelliferone.

32. The method of claim 31 wherein the medium further comprises 4-methylumbelliferone-β-D-glucuronide as a second fluorogenic substrate.

33. A rapid presence-absence method for determining when an original liquid or liquified sample contains less than one fecal coliform cell per 100 milliliters, comprising:

(a) filtering a first portion of the original sample upon a first filter for concentrating the live fecal coliforms in the first portion, filtering a second portion of the original sample upon a second filter for concentrating the live fecal coliform cells in the second portion, filtering a third portion of the original sample upon a third filter for concentrating the live fecal coliform cells in the third portion and filtering a fourth portion of the original sample upon a fourth filter for concentrating the live fecal coliform cells in the fourth portion;

(b) providing an actuating medium having a fluorogenic substrate which when metabolized by β-galactosidase yields a fluorescent product;

(c) providing a first sample container, a second sample container, a third sample container, a fourth sample container, a first control container, a second control container, a third control container, and a fourth control container, each containing a quantity of actuating medium therein;

(d) placing the first filter into the actuating medium contained in the first sample container, the second filter into the actuating medium contained in the second sample container, the third filter into the actuating medium contained in the third sample container, and the fourth filter into the actuating medium contained in the fourth sample container;

(e) providing an incubation means;

(f) incubating the first sample container and the first control container for a brief first duration;

(g) adjusting the pH of the first sample container and of the first control container to an alkaline pH after the first duration;

(h) irradiating the first sample container and the first control container, after adjusting the pH, with an excitation wavelength of light;

(i) incubating the second sample container and the second control container for a second duration;

(j) adjusting the pH of the second sample container and of the second control container to an alkaline pH after the second duration;

(k) irradiating the second sample container and the second control container, after adjusting the pH, with the excitation wavelength of light;

(l) incubating the third sample container and the third control container for a third duration;

(m) adjusting the pH of the third sample container and of the third control container to an alkaline pH after the third duration;

(n) irradiating the third sample container and the third control container, after adjusting the pH, with the excitation wavelength of light;

(o) incubating the fourth sample container and the fourth control container for a fourth duration;

(p) adjusting the pH of the contents of the fourth sample container and the contents of the fourth control container to an alkaline pH after the fourth duration;

(q) irradiating the fourth sample container and the fourth control container, after adjusting the pH, with the excitation wavelength of light;

(r) measuring, after each irradiation step, a first sample fluorescence value from the first sample container and a first control fluorescence value from the first control container, a second sample fluorescence value from the second sample container and a second control fluorescence value from the second control container, a third sample fluorescence value from the third sample container and a third control fluorescence value from the third control container, and a fourth sample fluorescence value from the fourth sample container and a fourth control fluorescence value from the fourth control container;

(s) using the first control fluorescence value and the first sample fluorescence value to obtain a correction factor;

(t) using the second control fluorescence value to adjust the second sample fluorescence value to obtain an adjusted second sample fluorescence value;

(u) using the third control fluorescence value to adjust the third sample fluorescence value to obtain an adjusted third sample fluorescence value;

(v) using the fourth control fluorescence value to adjust the fourth sample fluorescence value to obtain an adjusted fourth sample fluorescence value;

(w) using the correction factor to correct the adjusted second sample fluorescence value to obtain a corrected second sample fluorescence value;

(x) using the correction factor to correct the adjusted third sample fluorescence value to obtain a corrected third sample fluorescence value;

(y) using the correction factor to correct the adjusted fourth sample fluorescence value to obtain a corrected fourth sample fluorescence value; and (z) concluding that the original sample contains less than one fecal coliform cell per 100 milliliters when
  (1) the corrected second sample fluorescence value is positive and the corrected third sample fluorescence value is positive and is less than or equal to the corrected second sample fluorescence value, or
  (2) the corrected third sample fluorescence value is positive and the corrected fourth sample fluorescence value is positive and is less than or equal to the corrected third sample fluorescence value.

34. The method of claim 33 wherein the brief duration is less than about five minutes.

35. The method of claim 34 wherein the first duration is about two to five minutes.

36. The method of claim 33 wherein the second duration is from about one hour to about four hours.

37. The method of claim 33 wherein the third duration is from about two hours to about five hours with a proviso that the third duration is about one hour or more longer than the second duration.

38. The method of claim 33 wherein the fourth duration is from about three hours to about five hours with a proviso that the fourth duration is about one hour or more longer than the third duration.

39. The method of claim 33 wherein the first duration is in a range of from about two minutes to about 5 minutes, the second duration is about two hours, the third duration is about four hours, and the fourth duration is about six hours.

40. The method of claim 33 wherein the first duration is less than about 5 minutes, the second duration is about one to two hours, the third duration is in a range of from about three hours to about five hours, and the fourth duration is in a range of from about four hours to about six hours with a proviso that a third duration is at least about one hour longer than the second duration and the fourth duration is at least about one hour longer than the third duration.

41. The method of claim 33 wherein the second duration and the third duration differ by at least about one hour, the third duration and the fourth duration differ by at least about one hour, and the second duration and the fourth duration differ by at least about two hours.

42. The method of claim 33 wherein the step of obtaining the correction factor further comprises subtracting the first control fluorescence value from the first sample fluorescence value.

43. The method of claim 33 wherein the step of obtaining an adjusted sample fluorescence value further comprises subtracting the corresponding control fluorescence value from the sample fluorescence value.

44. The method of claim 33 wherein the step of obtaining a corrected sample fluorescence value further comprises subtracting the correction factor from the adjusted sample fluorescence value.

45. The method of claim 33 further comprising culturing a second portion of the original sample on an agar medium containing the actuating medium, incubating the culture medium in the incubation means for about seven hours, irradiating the culture medium after the incubation period with the excitation wavelength and counting a number of microcolonies visible on the culture medium.

46. The method of claim 45 further comprising applying an alkaline solution to the microcolonies for enhancing fluorescence prior to counting the microcolonies.

47. A rapid presence-absence method for determining when an original liquid or liquified sample contains less than one fecal coliform cell per 100 milliliters, comprising:

(a) filtering a first portion of the original sample upon a first filter for concentrating the live fecal coliforms in the first portion and filtering a second portion of the original sample upon a second filter for concentrating the live fecal coliform cells in the second portion and filtering a third portion of the original sample upon a third filter for concentrating the live fecal coliform cells in the third portion;

(b) providing an actuating medium comprising water, 4-methylumbelliferone-$\beta$-D-galactoside and
  about 0.46% to 0.54% by weight of a peptone,
  about 0.26% to 0.34% by weight of a yeast extract,
  about 0.4% to 0.6% by weight of an enzyme inducer,
  about 0.73% to 0.77% by weight of a salt,
  about 0.48% to 0.52% by weight of pyruvate,
  about 0.01% to 0.03% by weight of a surfactant, and
  about 0.009% to 0.011% by weight of bile salts;

(c) providing a first sample container, a second sample container, a third sample container, a first control container, a second control container, and a third control container, each containing a quantity of actuating medium therein;

(d) placing the first filter into the actuating medium contained in the first sample container, the second filter into the actuating medium contained in the second sample container and the third filter into the actuating medium contained in the third sample container;

(e) providing an incubation means;

(f) incubating the first sample container and the first control container for a brief first duration;

(g) adjusting the pH of the contents of the first sample container and the contents of the first control container to an alkaline pH after the first duration;

(h) irradiating the first sample container and the first control container, after adjusting the pH, with an excitation wavelength of light;

(i) incubating the second sample container and the second control container for a second duration;

(j) adjusting the pH of the second sample container and of the second control container to an alkaline pH after the second duration;

(k) irradiating the second sample container and the second control container, after adjusting the pH, with the excitation wavelength of light;

(l) incubating the third sample container and the third control container for a third duration;

(m) adjusting the pH of the third sample container and of the third control container to an alkaline pH after the third duration;

(n) irradiating the third sample container and the third control container, after adjusting the pH, with the excitation wavelength of light;

(o) measuring, after each irradiation step, a first sample fluorescence value from the first sample container and a first control fluorescence value from the first control container and a second sample fluorescence value from the second sample container and a second control fluorescence value from the second control container, and a third sample fluorescence value from the third sample container and a third control fluorescence value from the third control container;

(p) using the first control fluorescence value and the first sample fluorescence value to obtain a correction factor;

(q) using the second control fluorescence value to adjust the second sample fluorescence value to obtain an adjusted second sample fluorescence value;

(r) using the third control fluorescence value to adjust the third sample fluorescence value to obtain an adjusted third sample fluorescence value;

(s) using the correction factor to correct the adjusted second sample fluorescence value to obtain a corrected second sample fluorescence value;

(t) using the correction factor to correct the adjusted third sample fluorescence value to obtain a corrected third sample fluorescence value; and (u) concluding that the original sample contains less than one fecal coliform cell per 100 milliliters when the corrected second sample fluorescence value is positive and the corrected third sample fluorescence value is positive and is less than or equal to the corrected second sample fluorescence value.

48. The method of claim 47 further comprising culturing a second portion of the original sample on an agar medium containing the actuating medium, incubating the culture medium in the incubation means for about seven hours, irradiating the culture medium after the incubation period with the excitation wavelength and counting a number of microcolonies visible on the culture medium.

49. The method of claim 48 further comprising applying an alkaline solution to the microcolonies for enhancing fluorescence prior to counting the microcolonies.

50. The method of claim 47, wherein the enzyme inducer is lactose, the surfactant is sodium lauryl sulfate, the enzyme induced by the inducer is β-D-galactosidase, and the salt is NaCl.

51. The method of claim 47 wherein the actuating medium further comprises about 0.004% to 0.006% by weight of 4-methylumbelliferone-β-D-glucuronide.

52. A rapid direct count method for confirming when an original liquid or liquified sample contains less than one fecal coliform cell per 100 milliliters, the rapid direct count method to be used with a presence/absence test for fecal coliform bacteria wherein an absence determination is made when a first sample fluorescence value is positive and a second sample which is incubated for a predetermined duration longer than the first sample has a second sample fluorescence value which is positive and which is less than or equal to the first sample fluorescence value, the rapid direct count method comprising:

(a) filtering a portion of the original sample upon a filter;

(b) providing a culture medium comprising an actuating medium comprising:
   about 0.46% to 0.54% by weight of a peptone,
   about 0.26% to 0.34% by weight of a yeast extract,
   about 0.4% to 0.6% by weight of an enzyme inducer,
   about 0.73% to 0.77% by weight of a salt,
   about 0.48% to 0.52% by weight of pyruvate,
   about 0.01% to 0.03% by weight of a detergent,
   about 0.009% to 0.011% by weight of bile salts, and
   further comprising a quantity of 4-methylumbelliferone-β-D-galactoside for yielding 4-methylumbelliferone as a fluorescent product;

(c) contacting the filter with the culture medium, the culture medium contained within a container;

(d) providing an incubation means having a heat transference medium which maintains an intimate physical contact with each container disposed therein;

(e) incubating the culture container for a duration of about seven hours;

(f) irradiating the culture container after the incubation duration with a predetermined excitation wavelength of light; and (g) concluding that the original sample contains less than one fecal coliform cell per 100 milliliters when no fluorescent microcolony is visible on the culture container.

53. The method of claim 52 wherein the peptone is proteose peptone No. 3, the enzyme inducer is lactose, the salt is NaCl and the detergent is sodium lauryl sulfate.

54. The method of claim 52 wherein the actuating medium further comprises 0.004% to 0.006% by weight of 4-methylumbelliferone-β-D-glucuronide.

55. The method of claim 52 further comprising applying an alkaline solution to the microcolonies for enhancing fluorescence prior to counting the microcolonies.

56. A rapid presence-absence method for concluding when an original liquid or liquified sample contains less than one fecal coliform cell per 100 milliliters, comprising:

(a) filtering a first portion of the original sample upon a first filter for concentrating the live fecal coliforms in the first portion and filtering a second portion of the original sample upon a second filter for concentrating the live fecal coliform cells in the second portion;

(b) providing an actuating medium having a fluorogenic substrate which when metabolized by β-galactosidase yields a fluorescent product;

(c) providing a first sample container and a second sample container (d) exposing the first filter to a first quantity of the actuating medium in the first sample container and exposing the second filter to a second quantity of the actuating medium in the second sample container;

(e) providing an incubation means;

(f) incubating the first sample container for an first duration and the second sample container for a second duration longer than the first duration;

(g) adjusting the pH of the contents of the first sample container to an alkaline pH after the first duration;

(h) irradiating the first sample container, after adjusting the pH, with a predetermined excitation wavelength of light;

(i) adjusting the pH of the contents of the second sample container to an alkaline pH after the second duration;

(j) irradiating the second sample container after adjusting the pH, with the predetermined excitation wavelength of light;

(k) measuring, after each irradiation step, a first sample fluorescence value from the first sample container and a second sample fluorescence value from the second sample container;

(l) correcting the first sample fluorescence value to obtain a corrected first sample fluorescence value;

(m) correcting the second sample fluorescence value to obtain a corrected second sample fluorescence value; and (n) concluding that the original sample contains less than one fecal coliform cell per 100 milliliters when the corrected first sample fluorescence value is positive and the corrected second sample fluorescence value is positive and is less than or equal to the corrected first sample fluorescence value.

* * * * *

UNITED STATES PATENT AND TRADEMARK OFFICE
CERTIFICATE OF CORRECTION

PATENT NO. : 5,518,894

DATED : May 21, 1996

INVENTOR(S) : Berg

It is certified that error appears in the above-identified patent and that said Letters Patent is hereby corrected as shown below:

In the ABSTRACT, lines 7 and 8, please delete "After adjusting the pH is incubation to" and substitute therefor --After incubation the pH is adjusted to--.

Column 3, line 63, please delete "4.5° C" and substitute therefor --44.5° C--.

Column 7, line 38, please delete "4-methylumbelli-ferone-ß-D-glucuronide" and substitute therefor --4-methylumbelliferone-ß-D-glucuronide--.

Column 7, lines 40 and 41, please delete "4methylumbeoferpme-ß-D-glucurondie" and substitute therefor --4-methylumbelliferone-ß-D-glucuronide--.

Column 9, line 6, please delete "waste" and substitute therefor --Waste--.

Column 9, line 19, please delete "44.5° C. + 2° C." and substitute therefor --44.5° C. ± 2° C.--.

Column 9, line 53, please delete "44.5+0.2° C." and substitute therefor --44.5 ± 0.2° C.--

Column 10, line 22, please delete "Surfate" and substitute therefor --Sulfate--.

UNITED STATES PATENT AND TRADEMARK OFFICE
CERTIFICATE OF CORRECTION

PATENT NO. : 5,518,894

DATED : May 21, 1996

INVENTOR(S) : Berg

It is certified that error appears in the above-identified patent and that said Letters Patent is hereby corrected as shown below:

Column 14, line 38, please delete "of the contents".

Column 14, lines 49 and 50, please delete "in a predetermined manner".

Column 15, line 53, please delete "predetermined".

Column 15, line 54, please delete "predetermined".

Column 15, line 56, please delete "predetermined".

Column 15, lines 57 and 58, please delete "predetermined".

Column 15, line 65, please delete "of the contents".

Column 15, line 66, please delete "the contents".

Column 16, lines 2 and 3, please delete "a predetermined" and substitute therefor --an--.

Column 16, line 6, please delete "of the contents".

Column 16, line 7, please delete "the contents".

Column 16, line 11, please delete "predetermined".

Column 16, line 14, please delete "of the contents".

Column 16, line 15, please delete "the contents".

UNITED STATES PATENT AND TRADEMARK OFFICE
CERTIFICATE OF CORRECTION

PATENT NO. : 5,518,894  
DATED : May 21, 1996  
INVENTOR(S) : Berg

Page 3 of 5

It is certified that error appears in the above-identified patent and that said Letters Patent is hereby corrected as shown below:

Column 10, line 55 (Table 1), please delete "Protease" and substitute therefor --Proteose--.

Column 11, line 7 (Table 2), please delete "Protease" and substitute therefor --Proteose--.

Column 13, line 52, please delete "per milliliters" and substitute therefor --per 100 milliliters--.

Column 13, line 65, please delete "predetermined".

Column 14, line 2, please delete "incubating a" and substitute therefor --incubating the--.

Column 14, line 4, please delete "wherein a" and substitute therefor --wherein the--.

Column 14, line 5, please delete "in the range" and substitute therefor --in a range--.

Column 14, line 6, please delete "with the proviso" and substitute therefor --with a proviso--.

Column 14, line 7, please delete "a second duration" and substitute therefor --the second duration--.

Column 14, line 34, please delete "adjusting a pH of the contents of the" and substitute therefor --adjusting the pH of the--.

UNITED STATES PATENT AND TRADEMARK OFFICE
CERTIFICATE OF CORRECTION

PATENT NO. : 5,518,894
DATED : May 21, 1996
INVENTOR(S) : Berg

It is certified that error appears in the above-identified patent and that said Letters Patent is hereby corrected as shown below:

Column 16, line 19, please delete "predetermined".

Column 16, line 67, after "proviso that" please insert --the--.

Column 18, line 35, please delete "of the contents".

Column 18, line 36, please delete "the contents".

Column 19, line 37, please delete "a third duration" and substitute therefor --the third duration--.

Column 20, line 31, please delete "of the contents".

Column 20, line 32, please delete "the contents".

Column 21, line 38, please delete "predetermined".

Column 21, line 66, please delete "predetermined".

Column 22, line 34, please delete "for an first" and substitite therefor --for a first--.

Column 22, line 41, please delete "a predetermined".

UNITED STATES PATENT AND TRADEMARK OFFICE
CERTIFICATE OF CORRECTION

PATENT NO. : 5,518,894
DATED : May 21, 1996
INVENTOR(S) : Berg

It is certified that error appears in the above-indentified patent and that said Letters Patent is hereby corrected as shown below:

Column 22, line 46, please delete "predetermined".

Signed and Sealed this

Thirteenth Day of May, 1997

*Attest:*

BRUCE LEHMAN

*Attesting Officer*  *Commissioner of Patents and Trademarks*